United States Patent
Smith et al.

(10) Patent No.: US 7,686,755 B2
(45) Date of Patent: Mar. 30, 2010

(54) RADIATION THERAPY APPARATUS WITH SELECTIVE SHIELDING CAPABILITY

(75) Inventors: Peter C. Smith, Half Moon Bay, CA (US); Michael Klein, Menlo Park, CA (US); Heike Hausen, Redwood City, CA (US); Paul A. Lovoi, Saratoga, CA (US)

(73) Assignee: Xoft, Inc., Sunnyvale, CA (US)

( * ) Notice: Subject to any disclaimer, the term of this patent is extended or adjusted under 35 U.S.C. 154(b) by 787 days.

(21) Appl. No.: 11/471,277

(22) Filed: Jun. 19, 2006

(65) Prior Publication Data

US 2008/0009659 A1    Jan. 10, 2008

(51) Int. Cl.
  *A61N 5/00*    (2006.01)
(52) U.S. Cl. ......................................... 600/3
(58) Field of Classification Search ................. 600/1–8
  See application file for complete search history.

(56) References Cited

U.S. PATENT DOCUMENTS

| | | | |
|---|---|---|---|
| 5,090,043 A | 2/1992 | Parker et al. | |
| 5,153,900 A | 10/1992 | Nomikos et al. | |
| RE34,421 E | 10/1993 | Parker et al. | |
| 5,369,679 A | 11/1994 | Sliski et al. | |
| 5,422,687 A | 6/1995 | Tanaka et al. | |
| 5,422,926 A | 6/1995 | Smith et al. | |
| 5,452,720 A | 9/1995 | Smith et al. | |
| 5,528,652 A | 6/1996 | Smith et al. | |
| 5,566,221 A | 10/1996 | Smith et al. | |
| 6,033,357 A | 3/2000 | Ciezki et al. | |
| 6,077,213 A | 6/2000 | Ciezki et al. | |
| 6,309,339 B1 | 10/2001 | Ciezki et al. | |
| 6,319,188 B1 | 11/2001 | Lovoi | |
| 6,387,035 B1 | 5/2002 | Jung, Jr. et al. | |
| 6,464,626 B1 | 10/2002 | Peterson | |
| 6,626,816 B1 | 9/2003 | Ciezki et al. | |
| 6,725,081 B2 | 4/2004 | Ciezki et al. | |
| 6,752,752 B2 | 6/2004 | Geitz | |
| 2002/0032359 A1 | 3/2002 | Geoffrion et al. | |
| 2003/0149327 A1 | 8/2003 | Chin et al. | |
| 2005/0027156 A1 | 2/2005 | Pulido et al. | |
| 2006/0173235 A1 | 8/2006 | Lim et al. | |
| 2006/0241332 A1 | 10/2006 | Klein et al. | |
| 2007/0106108 A1 * | 5/2007 | Hermann et al. ............... 600/7 |
| 2007/0129592 A1 | 6/2007 | Lubock et al. | |
| 2007/0191667 A1 | 8/2007 | Lubock et al. | |
| 2007/0191668 A1 | 8/2007 | Lubock et al. | |

FOREIGN PATENT DOCUMENTS

EP    0867200    9/1998

* cited by examiner

*Primary Examiner*—Charles A Marmor, II
*Assistant Examiner*—Christine D Hopkins
(74) *Attorney, Agent, or Firm*—Thomas M. Freiburger

(57) ABSTRACT

Brachytherapy applicators incorporate various forms of selective shielding devices for controlling the direction and intensity of radiation directed at a patient's tissue. In some forms the applicators include a retractable sheath, in some a series of retractable fingers. In other forms the applicator, having an inflatable balloon, has a shield which is retractable from a position adjacent to the balloon or retracted from the balloon, or a shield can itself be inflatable, separately or together with the balloon.

16 Claims, 13 Drawing Sheets

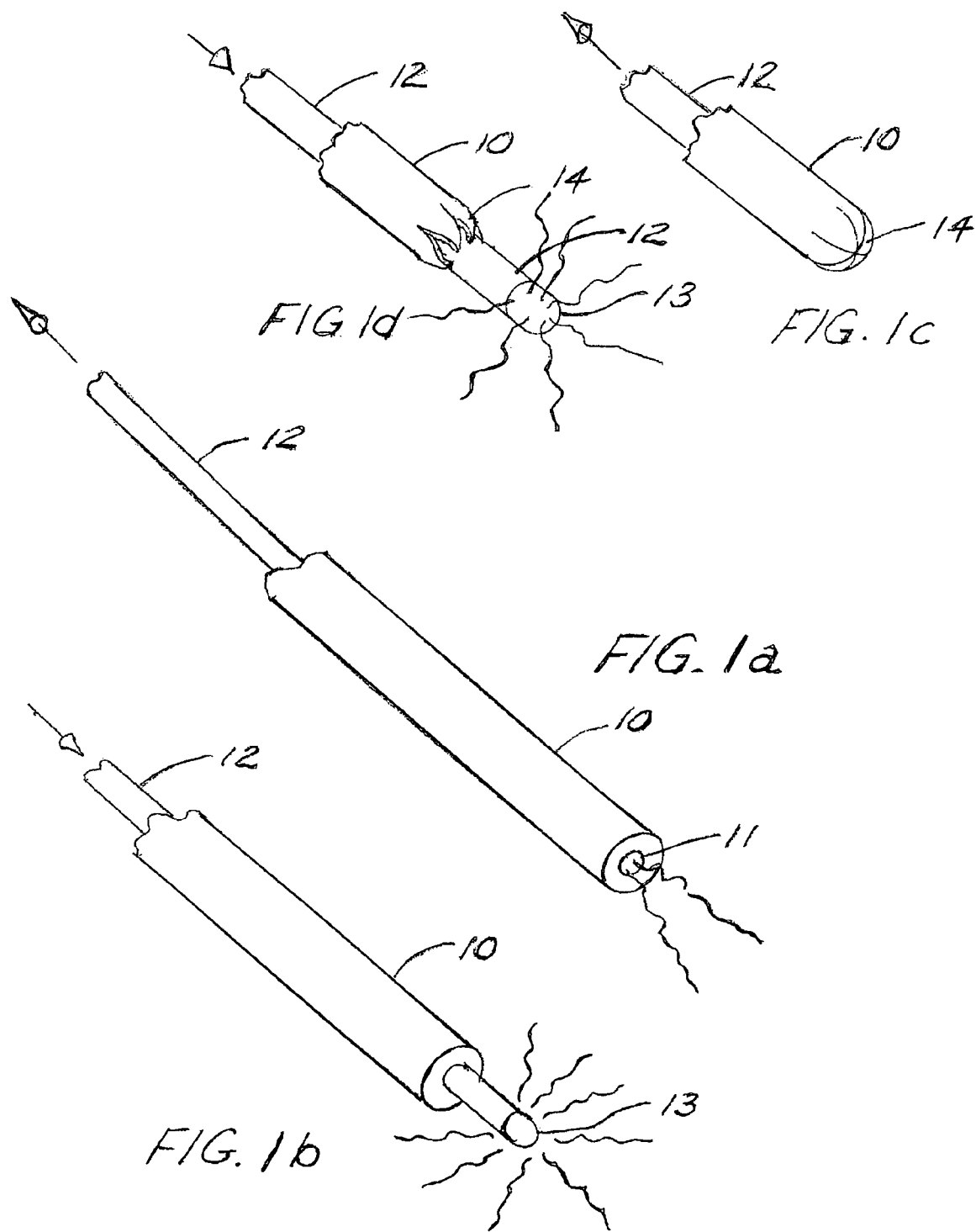

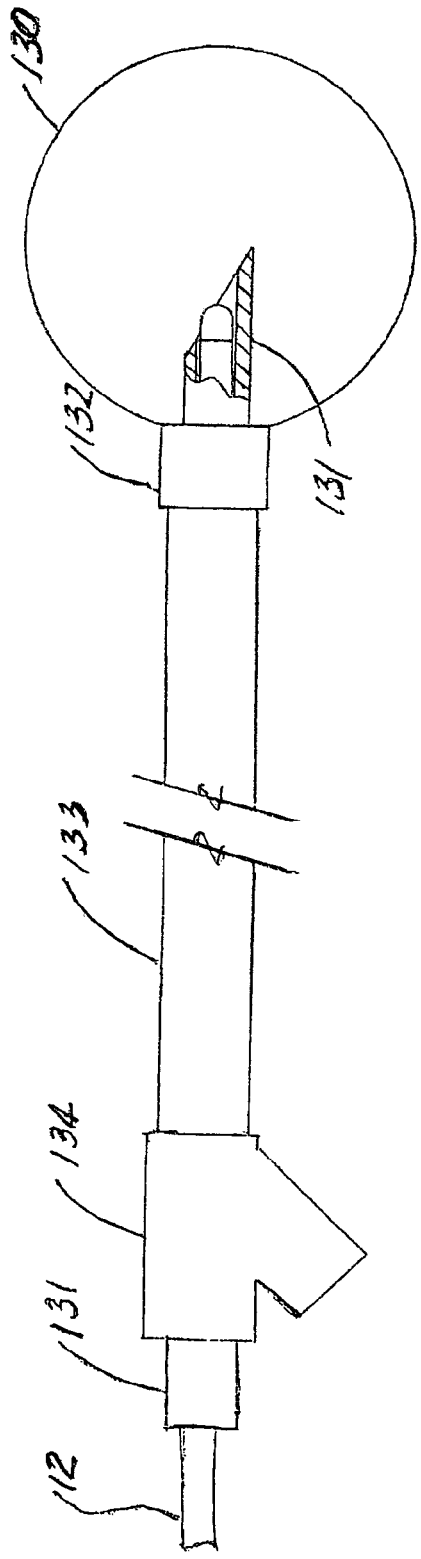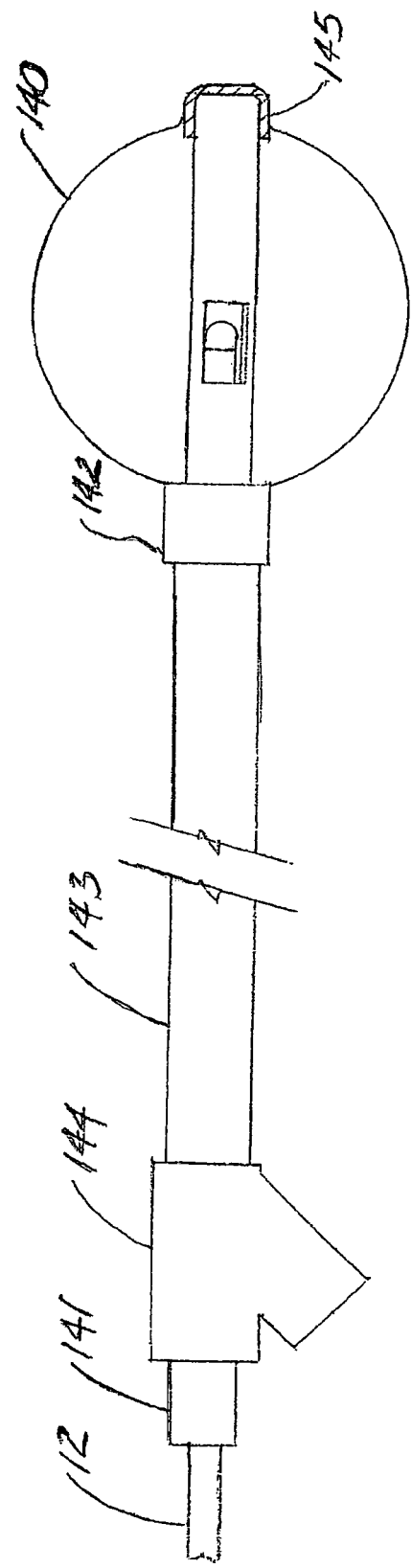
FIG. 12
FIG. 13

RADIATION THERAPY APPARATUS WITH SELECTIVE SHIELDING CAPABILITY

BACKGROUND OF THE INVENTION

The invention concerns shielding for radiation therapy source applicators, especially adjustable shielding for dynamic control of a radiation emission pattern.

Several forms of ionizing radiation therapy, particularly brachytherapy in which radiation is administered from a radiation source positioned within an anatomical cavity, are delivered using an applicator. Purposes for use of an applicator may include positioning the source within the cavity, mitigating radiation intensity incident on the cavity wall (radiation intensity decays exponentially with distance from the source), or tailoring cavity shape to facilitate radiation delivery in accordance with prescribed therapy parameters. Other purposes may also exist. The anatomical cavity may be a natural cavity, or may result from surgical intervention, for example as in the case of removal of a cancerous lesion.

Some applicators are essentially solid and of fixed configuration in that their shape doesn't vary during therapy. A typical fixed configuration applicator might comprise a catheter or wand, fashioned for placement within a body cavity, and into which a source, usually contained within a catheter, can be positioned. Such an applicator can be inserted into the body either through a natural orifice, or through a surgical incision or entry. Other forms of applicators may incorporate extensible elements which can be caused to alter shape after insertion into the body. A common form of the latter is a balloon applicator. Proxima Therapeutics Inc. of Alpharetta, Ga. (now part of Cytyc Corporation of Marlborough, Mass.) offers extensible applicators incorporating balloons. These applicator balloons are generally inflated with saline solution so as to attenuate radiation intensity near the source itself. With such an applicator, the source is ideally confined within a tube or channel within the balloon such that the position of the source within the outer skin or surface of the balloon is controlled and known. Preferably the shape of the inflated, extensible surface is coordinated with the radiation field of the source such that the intensity of radiation delivered just outside the surface of the balloon is uniform, below dangerous levels, but still strong enough to provide effective therapy.

Traditionally, the strength of the balloon, i.e. its rigidity or conformability, is chosen such that it shapes or tends to conform the tissues surrounding the cavity to the desired shape of the balloon as well to the radiation field expected from the source. When these factors can be simultaneously achieved, a uniform or isodose prescription can be delivered to the innermost tissues forming the cavity. When this is the case, the therapist can be assured of a uniform therapy throughout the target tissue adjacent the cavity. All too often, however, this condition cannot be produced. Sometimes the cavity cannot be reshaped such that the radiation intensity outside the balloon is insufficiently uniform. Should this situation arise, a balloon which conforms to the existing cavity might be employed, but then different measures must be taken to assure delivered dose uniformity. In other instances, nearby tissue structures may lie within the therapeutic range of the radiation outside the balloon, and so would be injured were a therapeutic dose of radiation delivered. In these instances, the therapist cannot deliver a preferred treatment unless measures are taken to avoid over-treatment of at-risk tissue. It is these measures to which this invention is addressed.

The radiation source is usually positioned within or near the distal tip of a catheter to facilitate handling of the source and positioning it within the applicator. The radiation source may be isotopic in nature or it may be electronic, producing x-rays which can be utilized to produce a therapeutic effect similar to isotopes. Isotope sources pertinent to use with balloon applicators are generally referred to as high dose sources and may be in the form of point sources, comprising a single isotope "seed", or they may be linear sources, comprising a series of seed sources, or a wire. When the source is a seed, multiple seeds or a wire, it is generally positioned in a catheter for insertion into the applicator in order to access the anatomical cavity to be treated. In other applications, the radiation source can be a fluid comprising radioactive material in suspension. This fluid can be used to inflate the extensible element of the applicator, rather than saline.

Radiation from radioisotopes is emitted in a known manner with a decaying intensity measured by the isotopes' half-life—the time at which half of their original intensity remains. Within practical time constraints, these parameters for a given radioisotope are fixed and they cannot be altered thus offering no possibilities for control. Furthermore, radioisotopes emit radiation at a few distinct energy bands, radiation from each band having its own ability to penetrate tissue and deliver dose. For example, the high-energy band of radiation emitted from $^{192}$Ir, the most common high dose-rate brachytherapy isotope, penetrates through large thicknesses of shielding materials. In addition, isotopes are always "on", so controlling the output with on/off switching is not possible. Other common and medically relevant radioisotopes also have emission spectra containing high-energy components that make selective shielding within a body cavity impractical due to space considerations. The radiation from these isotopes will penetrate any practical thickness of shielding material. This high-energy radiation easily penetrates well beyond the target site requiring therapy, thus delivering radiation to healthy parts of the body and risks injury. It also puts the therapist at risk, necessitating "bunker" type installations within which therapy can be conducted in the absence of attending personnel. This is a major disadvantage to the use of isotopic radiation in therapy.

In contrast, with electronically controlled radiation sources, the shape of the anode and its structure, and any minimal shielding utilized, determines the directionality of the x-rays emitted. Such an x-ray source is described in U.S. Pat. No. 6,319,188, the specification of which is incorporated herein in its entirety by reference. The emitted x-rays from such a source may be emitted isotropically, they may be directed radially, axially, or a combination thereof. Anode shaping is well known by those skilled in the art of x-ray generation apparatus. Anode shape, target thickness and target configuration can be used to change the radiation profile emitted from the miniature x-ray source. Also, miniature x-ray sources capable of producing the therapeutic effects of high dose rate isotopes only require thin radiation shields to selectively block emitted radiation, thus producing a directionally shaped radiation field. With electronically produced x-rays, the acceleration voltage determines the energy spectrum of the resulting x-rays. The penetration of the x-rays in tissue is directly related to the energy of the x-rays. The cumulative radiation dose directed at a point of the lesion may be controlled by x-ray source beam current or by "on" time within the body of the patient. Control of these parameters may be applied manually, or it can be automated in real-time based on matching output to a prescribed dose based on sensor feedback to a controller. An exemplary controlled system is described in patent application Ser. No. 11/394,640, filed Mar. 31, 2006, the disclosure of which is herein incorporated by reference in its entirety. This ease of control with x-rays and their minimal safety requirements are significant advantages to the therapist and the patient.

Therefore, in order to provide the therapist the ability selectively to protect radiation-sensitive or normal tissue structures from therapeutic dosages prescribed to treat diseased tissue, convenient apparatus and methods are needed which can be adapted to selectively shield these at-risk normal tissues while allowing prescribed dosages to adjacent, diseased tissue. The apparatus and methods of this invention provide the therapist this ability.

SUMMARY OF THE INVENTION

This invention comprises an array of shielding apparatus and methods which can be applied to solid (non-extensible) radiation therapy applicators. The invention further comprises apparatus and methods for use with applicators which incorporate an extensible element or elements, for example balloons. Some shielding embodiments are applicable to both types of applicator. Furthermore, in addition to being applicable to use of miniature x-ray sources for radiation therapy, they can be used with low dose rate isotopic sources where the emitted radiation can be effectively blocked by application of the shielding embodiments described.

As mentioned above, solid applicators may comprise flexible tubular sheaths or rigid wands, comprised of materials with minimal radiation attenuating properties, through the lumen of which a radiation source can be introduced and advanced into proximity of the tissue to be irradiated. If it is desired to shield a portion of the radiation output, radiation attenuating members may be incorporated into the catheter or applicator design, for example by providing an additional lumen or lumina within the sheath or wand shaft, through which a radiation attenuating member or members may be positioned adjacent the radiation source. By careful placement, the member or members may therefore be positioned to lie between the source and the tissue structures to be protected. The radiation attenuating members may be in fixed positions within the applicator relative to the catheter and/or source, or they may be moveable. Furthermore, if a plurality of attenuating members is employed, the members can be individually controlled or collectively controlled. If, for example, the members extend to the proximal end of the catheter or wand, control can be by hand manipulation, or by automatically actuated manipulation. Equally, manipulation can be indirect, for example by hydraulic actuation with pressure acting within the member lumen and acting against the proximal end of the member, assuming adequate seal between the member and lumen to achieve a piston effect.

If a single, tubular attenuating member is used, it can slide over the sheath or wand, or slide within the radiation source lumen, between the source and interior surface of the sheath. The attenuating member can be truncated angularly, or otherwise shaped, including comprising a window at its distal tip so as to produce the radiation output desired. If multiple attenuating members are employed, they can pass through individual lumina in the sheath or wand, or can be arrayed within an annular space inside the sheath lumen and outside of the source catheter. Each member may be shaped at its distal end in order to cooperate with adjacent members to produce the shielding effect desired. An exemplary shape of interest is both elongate and arcuate such that collectively, an array of adjacent members can be arranged to form a tube-like shield of attenuating material about the source within. Such an arrangement will substantially direct the radiation forward in the distal direction, with perhaps a lesser amount proximally toward the therapist (depending on applicator configuration), and very little radially. Alternatively, one or more of the attenuating "paddles" or finger-like shield segments can be individually retracted to produce circumferentially limited radiation output, directed radially. Such retraction can be constant, either open or closed. Equally, it can be cyclic, manually driven or automated, and can generate a rotating radiation path if desired.

Such an array, and the catheter and source, can extend beyond the distal end of the applicator sheath if desired. Proximal of the distal end of the sheath, the members or shield sections can transition from elongate arcuate paddles into round, wire-like extensions passing through applicator lumina and reaching the proximal end of the sheath, thereby permitting manipulation of the distal "paddles". The entire assembly could be operable within the sheath wall. With this arrangement, the distal end of the sheath or wand could optionally be closed, rather than open to the cavity. If distally, axially directed radiation is undesirable in such a case, the distal end of the sheath can be capped with radiation attenuating material which is heavily absorptive of radiation.

Another embodiment of interest is a pair of nesting, attenuating tubes operating within the lumen of the sheath, and surrounding the source catheter. The distal ends of the two tubes are castellated with sections cut from the ends such that when properly aligned, the circumferential shield is complete, blocking radial emission. Relative rotation of the tubes can produce a radial beam or beams of radiation. Alternatively, the tubes can have cooperating windows such that relative rotation opens a desired window or windows for release of radiation. Or, the tubes may be translated axially relative to one another, such that the axial length of the windows can be varied. If the relative position of the tubes is arranged to form a fixed window, the tubes may be translated and rotated to collectively irradiate a desired portion of the cavity tissue. See copending application Ser. No. 11/323,346, filed Dec. 30, 2005, the disclosure of which is included herein by reference, describing relatively movable windows in concentric tube shields.

In the embodiments discussed above, the shielding apparatus described is generally movable relative to the sheath body or shaft, comprised of a singular or a plurality of cooperating components and is independent of, but coordinated with, movement of the source catheter and source. The shield can be stationary, with the source movable axially.

In another embodiment, a solid applicator is comprised at least partially attenuating material, at least at the distal end of the sheath, so fashioned as to permit a radiation field having preferred shapes and characteristics dependent on the location of the source within the sheath. As a simple example, a tubular, attenuating shielding extension can be affixed to the distal end of the applicator sheath. The internal diameter of the extension can correspond to that of the sheath such that the source may be moved freely through the internal lumen of the assembly. The outer diameter of the extension, however, may be tapered or stepped, diminishing distally, such that the radiation delivered radially may be attenuated somewhat when the source is positioned distally, but more heavily attenuated when the source is positioned more proximally within the sheath assembly. Similarly, the solid tubular shield extension may be circumferentially notched or incomplete such that relatively unattenuated radiation emanates radially where portions of the shield are thin or missing, but purposely attenuated where they are all present. In such a fixed construction, the distal tip may or may not be blocked by attenuating material as suits the situation.

As stated earlier, attenuation apparatus may be fashioned for applicators with extensible or balloon elements, through which the therapeutic radiation passes. Most, if not all, of the shielding embodiments described above for use with solid applicators may be applied to balloon applicators as well, with the attenuating members functioning within or about the sheath or shaft onto which the balloon is affixed. In other respects, the description of these embodiments is similar, but the shielding portions of the embodiments operate within and are enclosed by the balloon. The balloon itself provides additional shielding opportunities, including opportunities to more precisely shape the intensity of the radiation field selectively.

When a balloon is being used as part of an applicator, the target zone for therapeutic radiation is generally a tissue volume all around the inflated balloon extending about one centimeter radially outwards from the surface of the balloon. It is this tissue which is generally thought to be most susceptible to recurrence of disease, especially cancer. For therapeutic purposes, a minimum intensity is required for cell destruction, and this minimum forms the basis for the prescription dose one centimeter outward from the surface of the balloon. As is known to those of skill in the art, radiation intensity decays exponentially as it passes through matter, therefore the intensity at the surface of the balloon will be greater than at the one centimeter target depth. It is important that the intensity at the balloon surface not be substantially greater than at target depth, however, since that would be overly destructive, and might risk injury to adjacent healthy tissue. At the surface of the source or source catheter, the intensity of the radiation is usually too high for therapeutic use.

Balloon applicator design utilizes the attenuating properties of the inflation medium in the balloon and the balloon membrane itself to attenuate radiation intensity from a high level at the source catheter to manageable intensity at the outer surface of the balloon. This is achieved by manipulation of attenuating properties of the inflation medium and balloon, and/or by the geometrical size and shape of the balloon. The useful effect of this technique is that the ratio of radiation intensity incident on the tissue at the balloon surface to the intensity one centimeter outward from the balloon is reduced, implying a more uniform dose throughout the target tissue. This phenomenon is called "beam hardening".

The absorption properties of the balloon membrane itself can be varied to tailor to suit the overall design situation. Balloon materials are usually polymers and are commonly polyurethane, PET, silicone rubber, or similar materials well known to those of skill in the art. The material of most balloon membranes is normally quite transparent to radiation, but their radiation attenuating properties can usually be tailored by loading them with attenuating fillers. Attenuating fillers such as barium sulfate and metallic particulates can be compounded into these balloon materials. Other fillers are also well known to those skilled in the art. The higher the filler loading generally, the more attenuating the resultant material, and the more rapid the exponential decay of the radiation incident upon it. In the end, total attenuation of a material is a function of both its attenuation properties as well as the thickness over which those properties block the path of the radiation. Therefore, a weakly attenuating but thick material may be equally effective at shielding tissue from radiation as a thin but strongly attenuating material.

In addition to material composition modifications to the balloons, their construction can be altered as well. For example, the wall thickness of the balloon membrane can be varied selectively during the manufacturing process. Thickness variations can result from molding design, or they can result from fabrication of balloon using materials of dissimilar thicknesses. Fabrication of materials of similar thickness, but different filler loadings may also be used to selectively shield specific balloon areas. See also applications Ser. No. 10/683,885 (filed Oct. 13, 2003) and Ser. No. 10/962,247 (filed Oct. 8, 2004) regarding attenuating balloons. The disclosures of both copending applications are included herein by reference.

As described above, the balloon may serve the further purpose of mechanically shaping the cavity by virtue of the pressure within the balloon. If the shaped cavity corresponds to the source intensity pattern, uniform dosage as prescribed is a relatively simple matter. In instances where the cavity either has a free-form shape or cannot be formed into a preferred shape, a balloon having elastic behavior (cavity filling) may be preferred in order to avoid air gaps outside the balloon adjacent the tissue forming the cavity. Such balloons may be of many of the same but the more elastic of the membrane materials outlined above, but probably with lesser wall thicknesses. Fillers can be similarly compounded into the material, or fabrication techniques can again be used to tailor attenuation. What is not under control where balloon behavior is elastic is the distance to target tissue from the source. Care must be taken to assure that the intensity of delivered radiation remains between the prescribed level and the danger level over the total balloon surface. Thicknesses may also be varied, but the problem becomes very complex because irregular expansion of the balloon alters the membrane thickness as well as its loading of filler per unit area, and hence its attenuating properties. Generally, the greater the distance the balloon expands, the thinner the membrane in that area.

In use of either solid or balloon applicators, either those of the invention, or prior art applicators, it may be desirable to provide shielding for the therapist in the proximal direction along the shaft of the wand or catheter. Particularly when the applicator is in use near a body opening, radiation may escape proximally along the shaft out of the patient toward where the therapist is likely to be positioned. When such exposure is likely, a local shield may be employed which is mounted on the applicator shaft to shield in the proximal direction. This embodiment may be solid sort of flange, and overlap the body opening sufficiently to block any such radiation effectively. Alternatively, it may fit within the body opening, forming a radiation seal in concert with the opening. Further, it may comprise an inflatable element independent of or integral with the main inflatable element of the applicator. Still further, on a balloon applicator, it can comprise a shielding member or attenuating segment at the proximal end of the primary applicator balloon such that it is automatically deployed when the applicator is put into use, and is of adequate scope or projection to prevent outwardly directed radiation toward the therapist.

These and other features and advantages of the present invention will become apparent from the following detailed description of preferred embodiments which, taken in conjunction with the accompanying drawings, illustrate by way of example the principles of the invention.

DESCRIPTION OF THE DRAWINGS

FIG. 1a is a perspective view of the tip of a solid applicator with an open tip, and having a source catheter positioned within emitting axially directed radiation at the tip.

FIG. 1b is a perspective view of the embodiment of FIG. 1a, but with the source catheter advanced and emitting radiation isotropically.

FIG. 1c is a perspective view of the tip of the embodiment of FIG. 1a, but with a closed tip which can be opened by advancement of the source catheter of FIG. 1a.

FIG. 1d is a perspective view of the tip of the embodiment of FIG. 1c, but with the source catheter advanced and emitting radiation.

FIG. 2c is a section taken through the shaft of the applicator of the embodiment of FIG. 2a.

FIG. 12 is a side elevation view of a balloon applicator having a one-part shield similar to that of FIG. 5.

FIG. 13 is a side elevation view of a balloon applicator having a one part shield similar to that of FIG. 6 with the applicator sheath affixed to the balloon at two points.

DESCRIPTION OF PREFERRED EMBODIMENTS

Figure 2C:
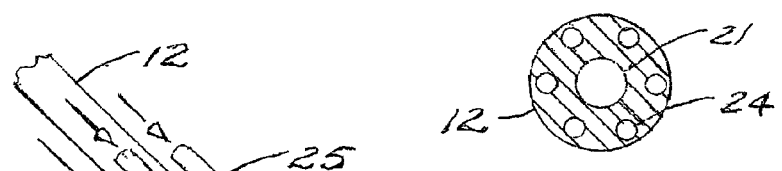

The figures generally illustrate the shielding embodiments of the present invention wherein the shielding serves to selectively protect certain tissue structures while not interfering with prescribed radiation therapy. In the drawings, the straight sheath or shaft of the applicators illustrated are shown shorter than they would in fact be. Furthermore, balloons are depicted as being transparent in order to more clearly illustrate apparatus within the balloons.

FIG. 1a shows a simple, solid, tubular attenuating applicator 10 having an open end 11, into the lumen of which is inserted a source catheter 12. Depending on the source and catheter characteristics, radiation can be emitted from the distal end. The degree of collimation will depend on the depth of the source within the applicator lumen. Such an applicator can be fashioned from a polymer like polyurethane, polypropylene, or a metal like stainless steel. In general, at least with electronic radiation sources, most metallic shielding totally absorbs any incident radiation in the range of interest for brachytherapy. If polymeric, attenuation can be controlled by filler additions into the material from which the applicator is made. Typical fillers might include barium sulfate or tungsten or stainless steel powder. Generally, the greater the filler component, the greater the degree of attenuation in the resulting filled material. In design, this applicator need be nothing more than a tube, perhaps extruded if polymeric, and drawn or machined if metallic.

FIG. 1b illustrates how such an applicator 10 as shown in FIG. 1a might function when the source 13 is advanced to a position distal of the end of the applicator shaft. In this case, the radiation is shown as if the source is essentially isotropic, emitting radiation throughout generally a spherical envelope.

FIG. 1c shows a variation of the applicator 10 of FIG. 1a, but with a closed tip which is separated into segments 14 which can hinge out of the way of the source catheter 12 as it is advanced. In this way, the embodiment shown is self-closing and can completely close off radiation when the catheter is withdrawn within the applicator rather than emitting radiation distally out of an open tip as in FIG. 1a. When the source and catheter are advanced, however, the tip opens by the segments hinging as shown in FIG. 1d, permitting radiation emission as in FIG. 1b. This can be accomplished with a polymeric material that tends to retain and to return to a preferred shape as in FIG. 1c.

Figure 2A:
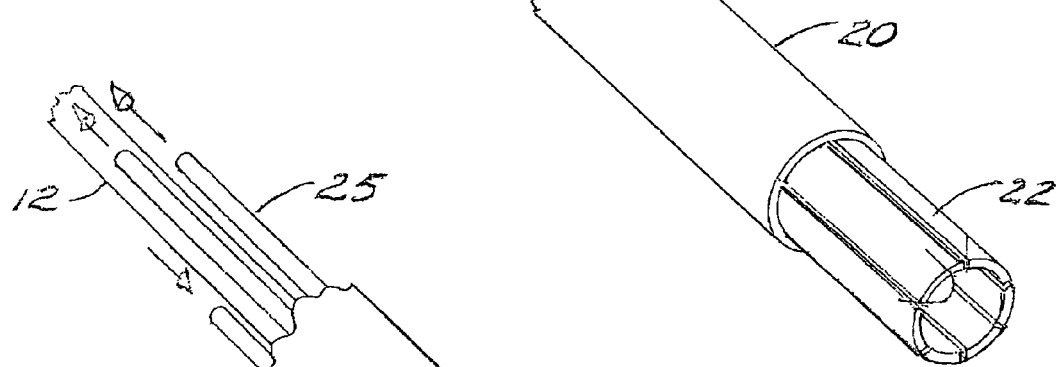
FIG. 2a is a perspective view of the tip of a solid applicator having "paddle" shaped shielding elements deployed circumferentially at the tip of the applicator sheath, and showing proximal extensions of the shielding members for axial manipulation of the elements from outside the patient, and with an axially shielded source catheter positioned within the shielding members.
Figure 2B:
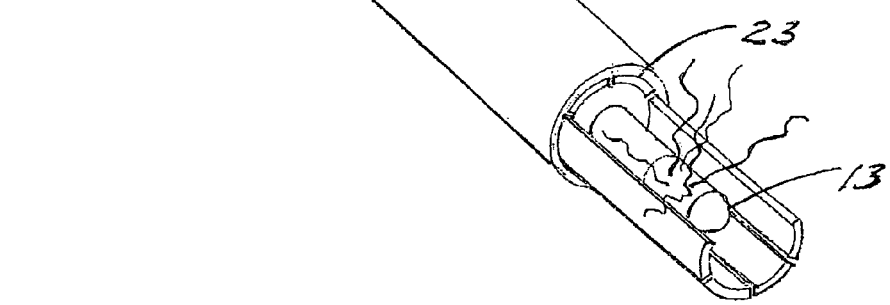
FIG. 2b is a perspective view of the applicator tip of the embodiment of FIG. 2a with two of six shielding elements retracted and partially exposing the top side of the source catheter in order to emit radiation radially over a portion of the applicator circumference.

FIGS. 2a-2c show an applicator 20 having a central lumen 21 for positioning the source catheter 12 centrally within the applicator 20. The applicator 20 also has satellite lumina 24 for positioning and manipulating paddle-like attenuation members or fingers 22 positioned in slots 23 within the wall of the shaft or sheath of the applicator tip, into which the paddles can be partially or completely retracted. Paddles 22 have rod like proximal extensions 25 operating in lumina 24 which can be used to manipulate the paddles or fingers from outside the patient's body, as indicated by the axial arrows. Alternatively, the paddles 22 and source 13 can function completely within the envelope of the applicator, never emerging axially from the tip of the applicator. In this embodiment, the applicator sheath 20 is fashioned from a polymer as described above, but with minimal attenuating filler, and more preferably without filler. The paddles are made of filler loaded, attenuating polymer such as that described above. They could also be metallic. In operation, retraction of selective paddles as shown in FIG. 2b will allow radiation emission in selective sectors around the circumference of the applicator. When positioned to act in concert, all radial emissions can be blocked or absorbed. Radiation can be swept rotationally by active use of the shielding members.

FIG. 2c shows a cross section through the shaft or sheath of the applicator 12. The lumina 24 for operating the paddles 22 are arranged as satellites around the central lumen 21 through which the source and its catheter are passed. It must be appreciated that other than paddle shapes can be employed without departing from the scope this invention.

Figure 3A:
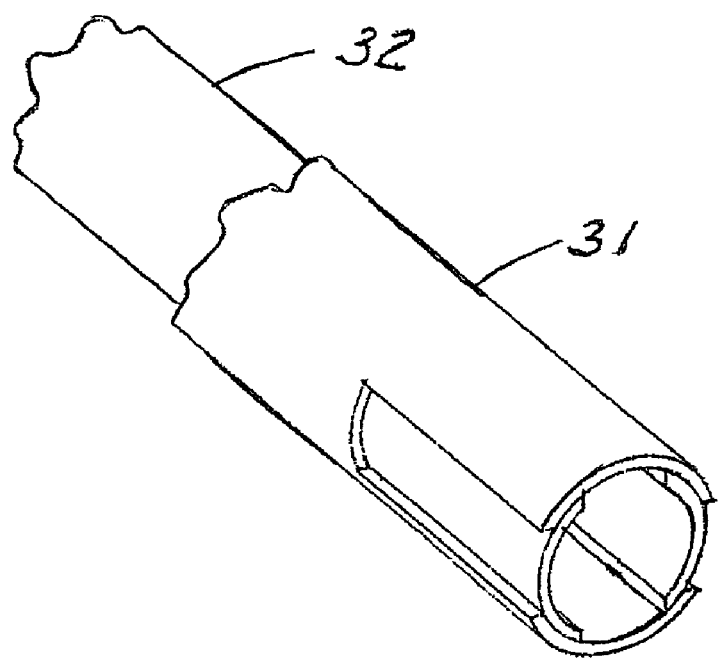
FIG. 3a is a perspective view of the tip of a two-part, coaxial attenuation embodiment to be positioned over the source catheter but within the sheath lumen, having castellated ends that in this view are so rotated as to act in concert to shield radial radiation completely.
Figure 3B:
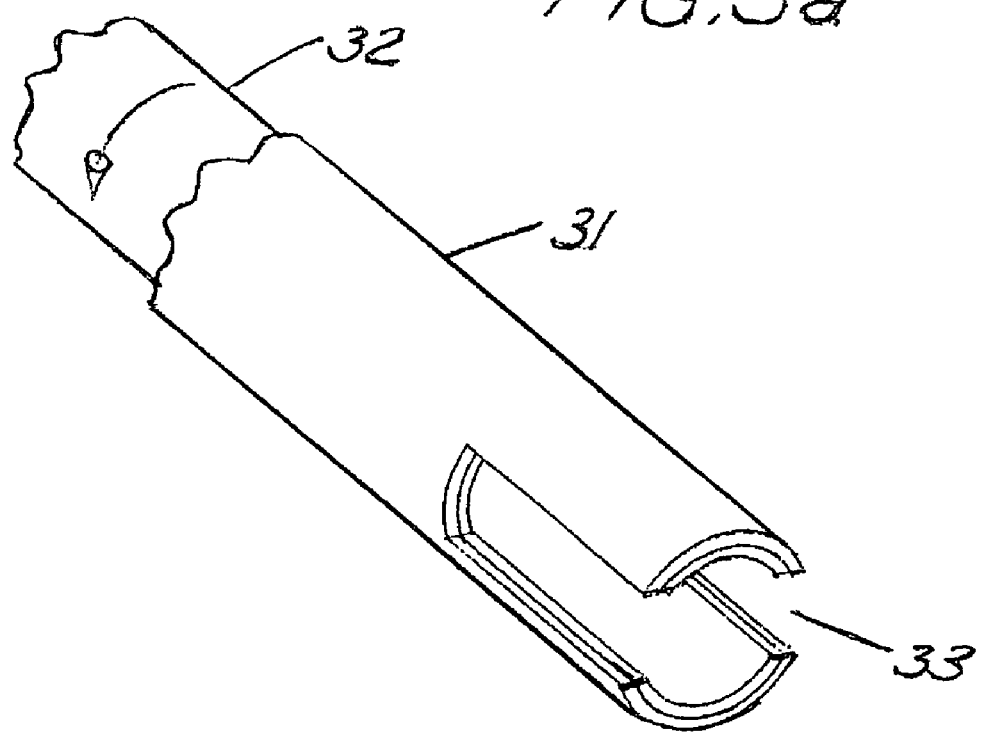
FIG. 3b is a perspective view of the embodiment of FIG. 3a, but with the two parts so rotated as to permit two opposed beams of radiation radially.

FIG. 3a depicts a pair castellated tubes 31 and 32 designed to operate within the central lumen of the applicator (not shown), but generally surrounding the source catheter (not shown). When the tubes are positioned as shown in FIG. 3a, all radial emission is blocked. When positioned as shown in FIG. 3b, circumferential segments 33 of the applicator emit radiation. At intermediate relative rotations, those segments are narrower than when fully open, as shown. In the embodiment shown, the castellation notches are rectilinear. They could equally be other shapes to suit a given situation without departing from the invention. The materials for the two tubes is preferably metallic, or alternatively attenuating polymers containing fillers as described previously.

Figure 4A:
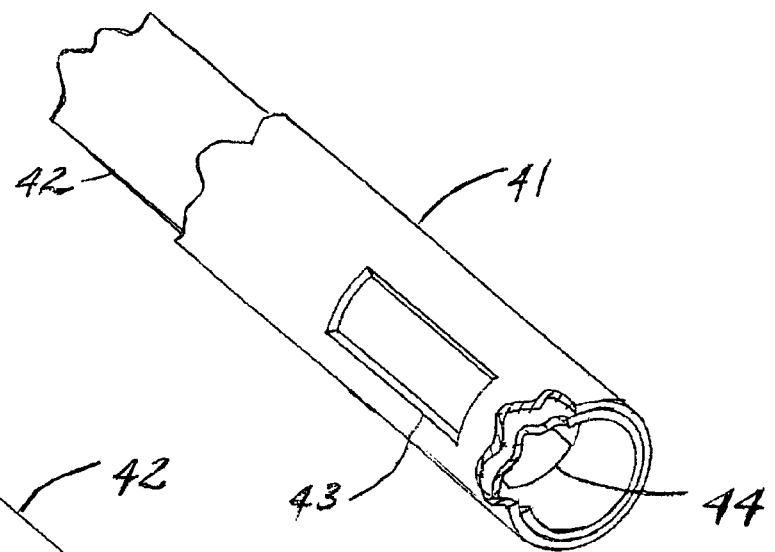
FIG. 4a is a perspective view in partial section of the tip of a two-part attenuation embodiment, with open tip, to be positioned over the source catheter, each part having a window and the windows shown so rotated as to block all radial radiation emission.
Figure 4B:
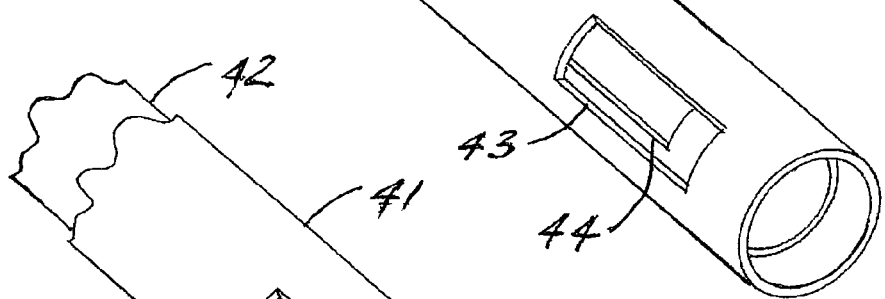
FIG. 4b is a perspective view of the embodiment of FIG. 4a, but with one window rotated and translated such that the window is partially open.
Figure 4C:
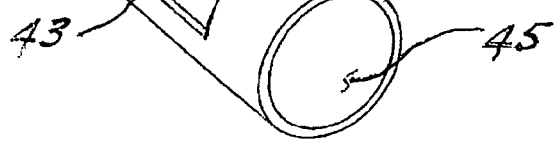
FIG. 4c is a perspective view of the embodiment of FIG. 4a, but with the tip of the inner part capped to prevent radiation emissions distally.

The embodiment shown in FIGS. 4a and 4b generally corresponds to that of FIGS. 3a and 3b, but rather than notches in the ends of the tubes, each tube 41, 42 has a window 43, 44 which can be positioned to cooperatively restrict the beam of radiation allowed to exit the applicator. The beam can be restricted axially by axial adjustment of one tube relative to the other, and it can be limited circumferentially by relative rotation (see arrows). Depending on the attenuation properties chosen, the beam can be partially blocked (one tube thickness of attenuation) or not attenuated (open window). By blocking the end of one or both tubes, by a disc 45 integral with tube 42 for example, axial (distal) radiation can be blocked as well.

Figure 5:
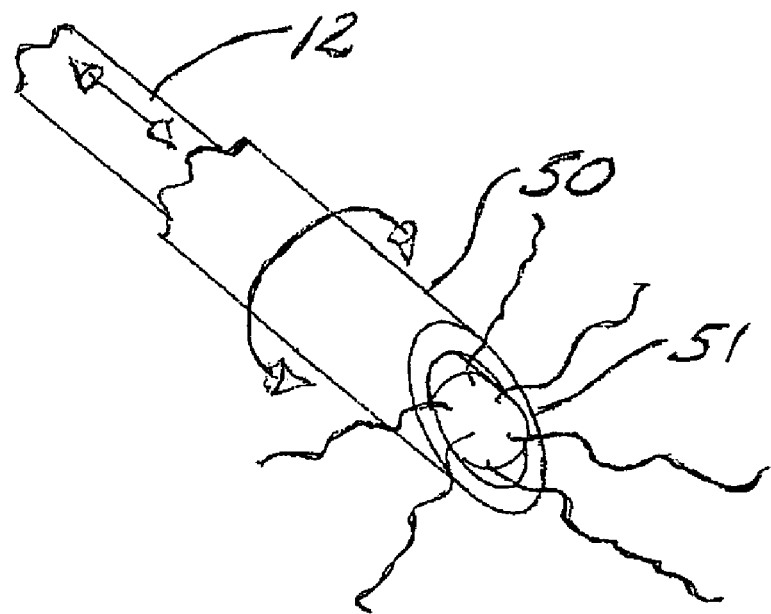
FIG. 5 is a perspective view of a one-part attenuation embodiment to operate within the applicator sheath and over the source catheter, having an angularly truncated distal tip, and with a source catheter shown within, such that directional radiation is provided.
Figure 6:
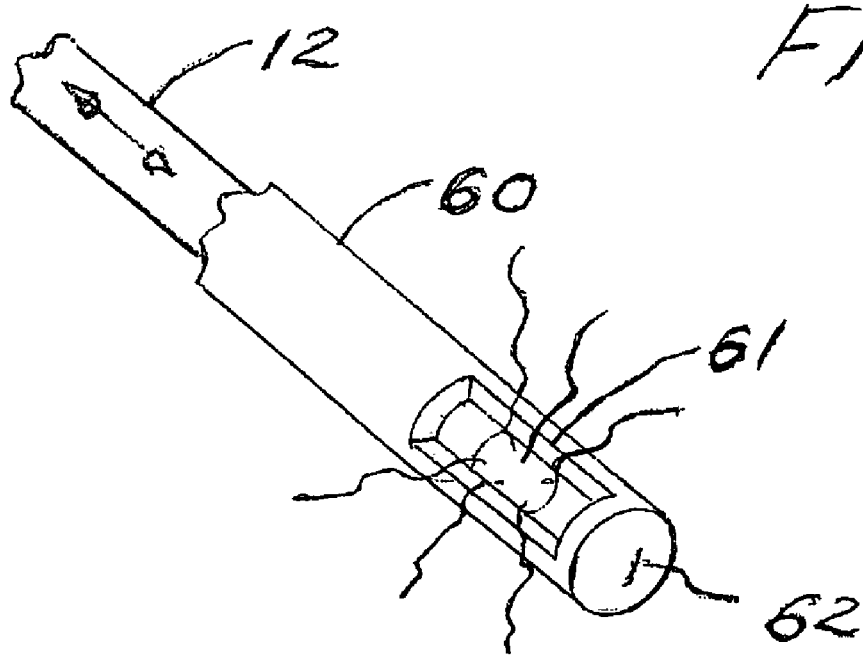
FIG. 6 is a perspective view of another one-part embodiment as in FIG. 5, but having a window through which radiation can emanate so as to provide directional radiation.

FIGS. 5 and 6 show one-part shield embodiments 50, 60 that comprise tubes which can be manipulated (see arrows) to operate within the applicator lumen (not shown) and outside of the source catheter 12, or alternatively outside the applicator shaft or sheath, or still further, can comprise the applicator sheath itself. The end can be shaped arbitrarily to suit the situation at hand. FIG. 5 shows a truncated, obliquely angled tip 51 whereas FIG. 6 shows a window 61 which can optionally have a sealed tip 62 (as shown). With such a shielding apparatus, the materials of construction are preferably attenuating.

Figure 7:
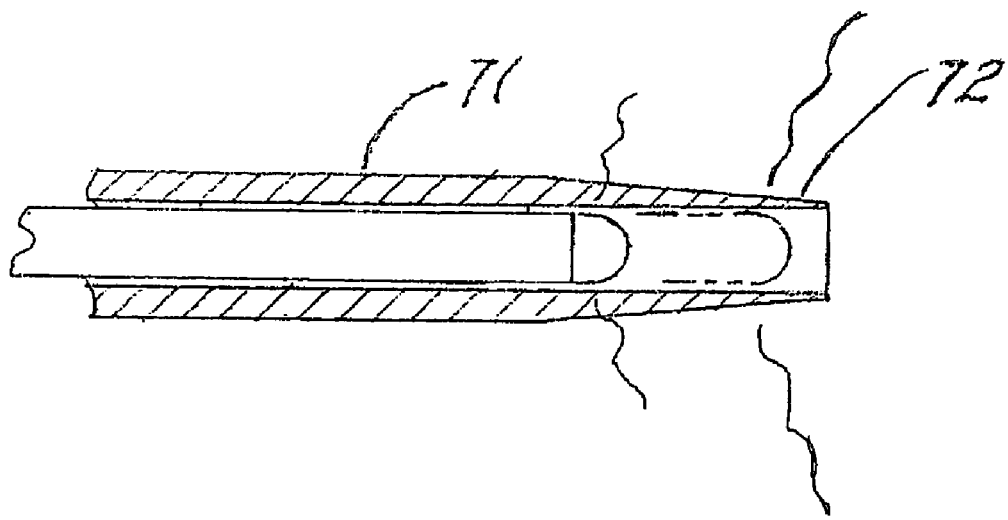
FIG. 7 is a cross sectional view of the tip of a one-part attenuating sheath having a tapered distal tip to provide varied attenuation.
Figure 8:
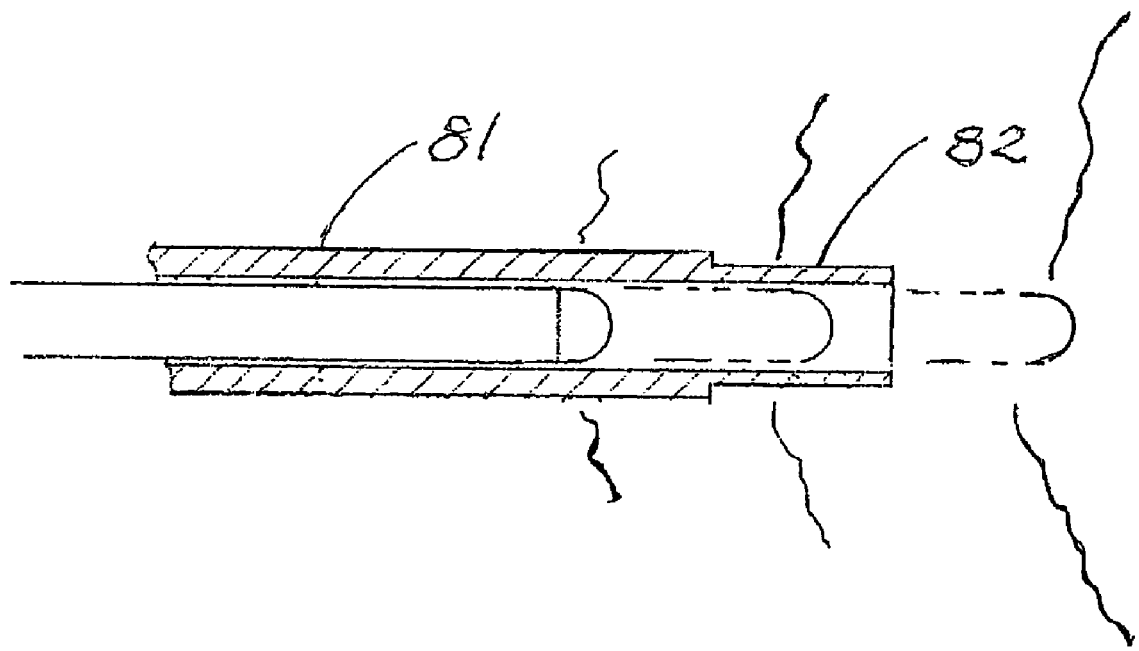
FIG. 8 is a cross sectional view of the tip of a one-part attenuating sheath having a stepped distal tip to provide varied attenuation.

FIGS. 7 and 8 show applicator tips 71, 81 which have graduated levels of shielding attenuation along their length by virtue of their geometry—the more distal, the less attenuating. In the embodiments shown, one tip 72 is tapered (FIG. 7), and the other tip 82 stepped (FIG. 8). If the source is positioned near the distal tip of the applicator, the radial radiation is more intense. if more proximal, the radiation is less intense. The tip may be open (as shown) or optionally sealed to prevent axial emission.

Figure 9:
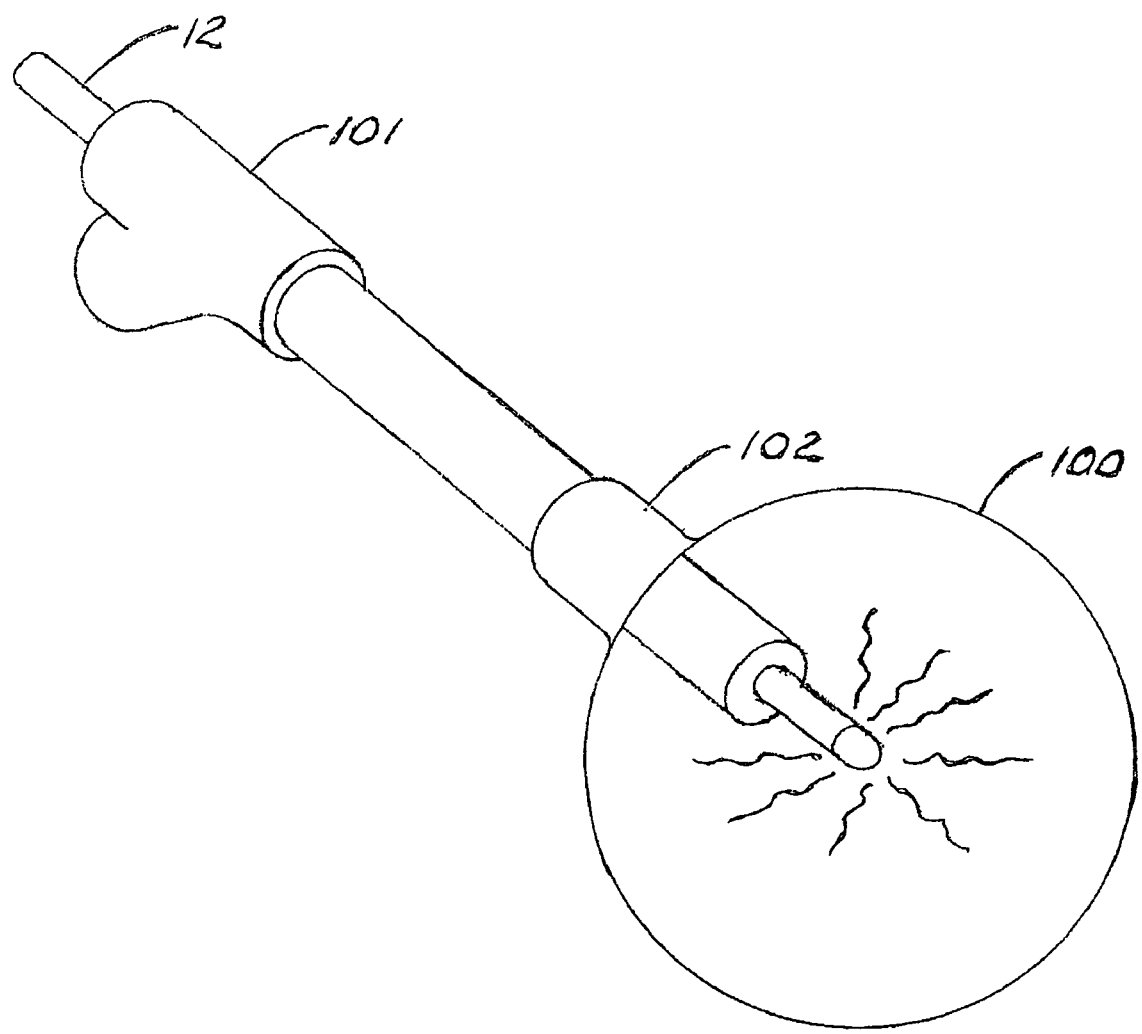
FIG. 9 is a perspective view of an applicator similar to that of FIG. 1b but including a balloon.

FIG. 9 depicts a balloon applicator apparatus corresponding in part to the applicator described in FIGS. 1 a, b, but having a balloon 100 affixed to the shaft or sheath of the applicator at point 102. A conventional hub 101 is affixed to the proximal end of the applicator shaft or sheath in order to provide for both source catheter 12 introduction through the in-line port which is fitted with seals (not shown) to prevent balloon leakage past the catheter shaft, and for inflation of balloon 100 through the auxiliary port, a connecting lumen within the wall of the applicator shaft, and through a port in the shaft into the balloon. The elements of the inflation circuit are not detailed since they are standard within the industry.

Figure 10:
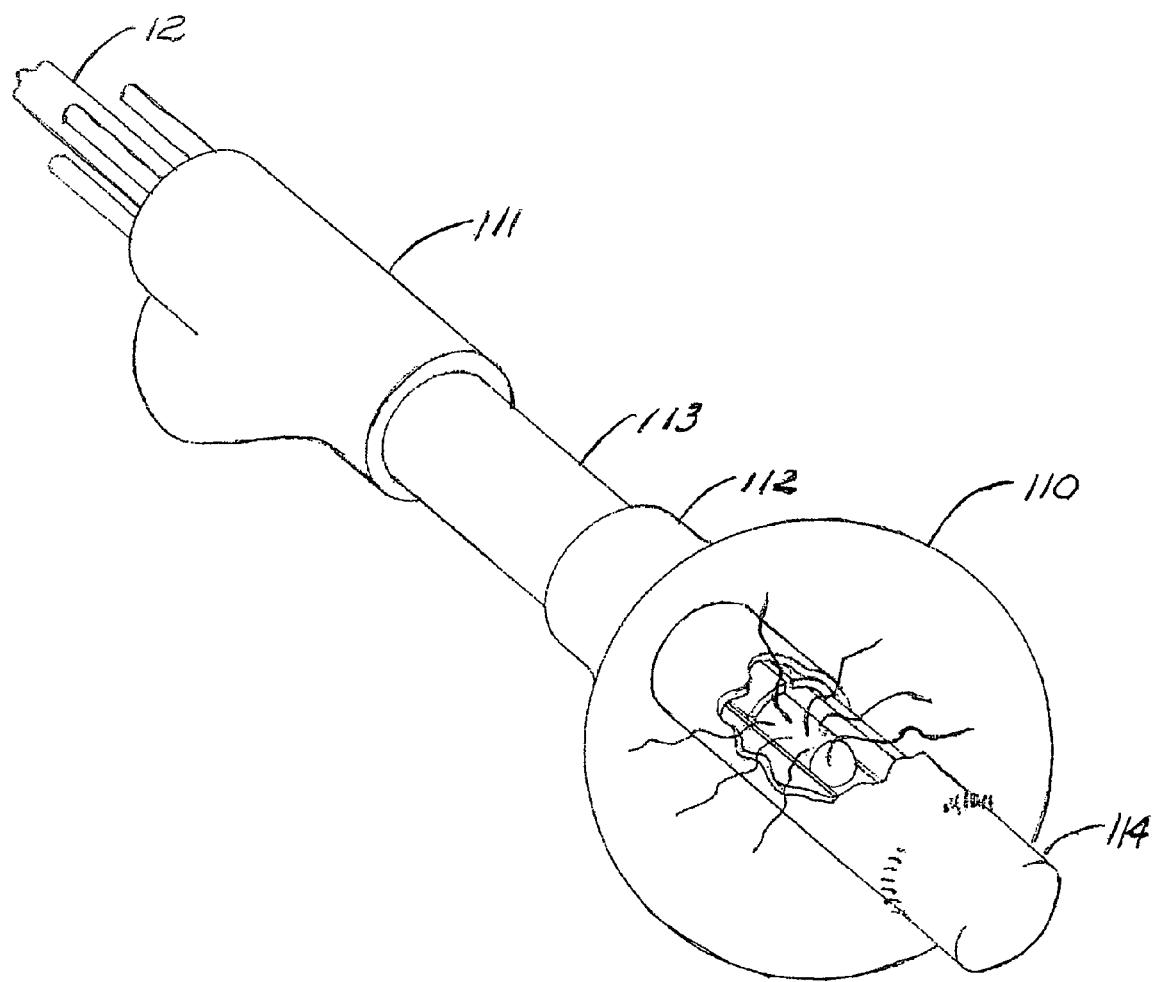
FIG. 10 is a perspective view of an applicator similar to that of FIG. 2b but including a balloon with the applicator affixed to the balloon at two points.

FIG. 10 depicts a balloon applicator apparatus corresponding in part to the applicator described in FIGS. 2a-2c, but having a balloon 110 affixed to the shaft or sheath of the applicator 113 at point 42. A conventional hub 111 is affixed to the proximal end of the applicator shaft or sheath, as above.

Figure 11:
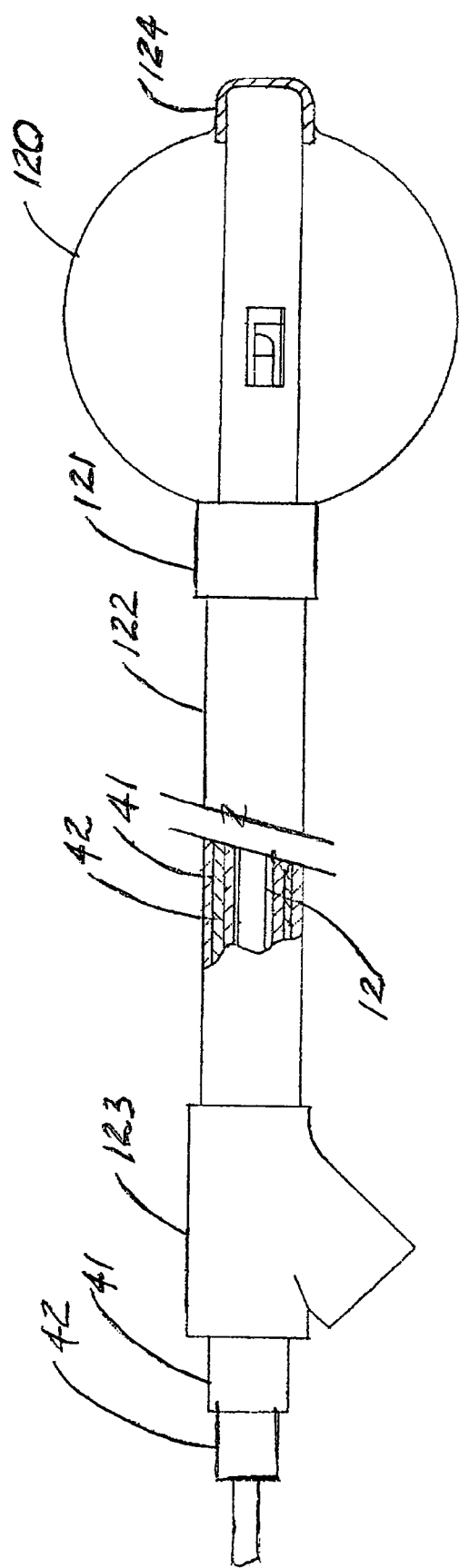
FIG. 11 is a side elevation view with partial sectioning showing a balloon applicator having a shielding apparatus similar to that of FIG. 4b and with the applicator sheath affixed to the balloon at two points.

FIG. 11 depicts a balloon applicator apparatus incorporating shielding elements similar to those of FIGS. 4a, b, but having a balloon 120 affixed to the applicator shaft at point 121 on applicator shaft 122. Within applicator shaft lumen, but outside the source catheter 12, are the two tubular shielding tubes 41 and 42 each having windows 43 and 44, and extending distally to be received by cup 124, providing rotating fixation of the balloon 120 relative to the applicator axis at two points. At the proximal end of the applicator shaft is a conventional hub 123. The source catheter and shielding tubes all pass concentrically through the straight port, with conventional seals (not shown) between adjacent parts to prevent balloon leakage. The auxiliary port is for inflation of the balloon 120 through a connecting lumen within the wall of the applicator shaft, and a port in the shaft into the balloon. The elements of the inflation circuit are not detailed since they are standard within the industry.

FIG. 12 depicts applicator apparatus having a truncated, oblique shield sleeve 131 similar to that described in FIG. 5, but with a balloon 130 affixed to applicator sheath 133 at a point 132. A conventional hub 134 is affixed to the proximal end of applicator sheath 133 to provide for introduction of the source catheter 12 and the shield sleeve 131, each of which must be properly sealed. The auxiliary port is for inflation of balloon 130 through this port, a connecting lumen within the wall of the applicator shaft, and through a port in the shaft into the balloon. The elements of the inflation circuit are not detailed since they are standard within the industry.

FIG. 13 depicts applicator apparatus having a shield sleeve 141 with window, similar to that described in FIG. 6, but with its distal tip extended, and a balloon bonded or otherwise affixed to the applicator shaft 143 at a point 142. The distal extension of shield sleeve 141 cooperates with a balloon mounted cup 145 to provide a rotational fixation between sleeve 141 and balloon 140, thus providing two point balloon fixation as previously described. A conventional hub 144 is affixed to the proximal end of applicator shaft 143 to provide for introduction of the source catheter 12 and the shield sleeve 141, each of which must be properly sealed. The auxiliary port is for inflation of balloon 140 through this port, a connecting lumen within the wall of the applicator shaft, and through a port in the shaft into the balloon. The elements of the inflation circuit are not detailed since they are standard within the industry.

Figure 14:
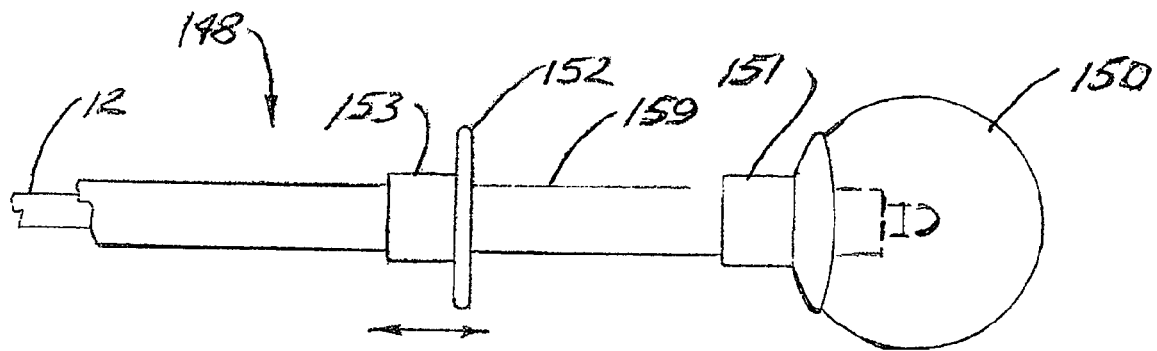
FIG. 14 is a side elevation view showing two axially shielding embodiments to attenuate proximally directed radiation, the one at right being a shielding section molded as part of the balloon or affixed on the balloon during or after balloon manufacture, and the embodiment at left being a solid attenuating flange with hub mounted slidably on the shaft of the applicator.
Figure 15:
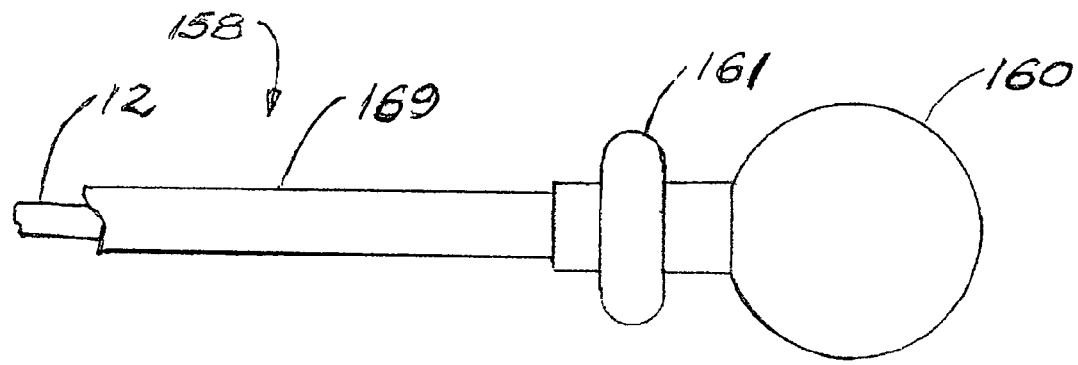
FIG. 15 is a side elevation view of a balloon applicator having an inflatable, attenuating balloon collar as an integral part of and proximal to the main applicator balloon.

FIG. 14 depicts a balloon applicator 148 having two alternate shielding apparatus for preventing, or at least attenuating, radiation directed along the applicator shaft 159, proximal of a balloon 150. To the right is an attenuating portion 151 of the balloon itself. This portion can be an integral portion of the balloon, with a hub as shown, or alternately without a hub, either molded in place or bonded to the balloon after or as part of fabrication, or as a segmental part of the balloon itself and included in the fabrication process. Preferably it is of polymer and filled with attenuating filler as previously described and sufficiently flexible so as to expand with the balloon upon inflation. To the left in FIG. 15 is a stand-alone flange 152 with collar 153 to affix the flange to the applicator shaft, as an alternate embodiment. The flange is solid and is optionally movable along the applicator shaft 159 (see arrow) by a sliding fit tight enough to retain its set position, or alternately having a conventional clamp or bonded fastening. The flange material is preferably a filled polymer, but could be metallic.

FIG. 15 depicts a balloon applicator 158 having a balloon 160 which in turn has an integral inflatable torus 161 located on an applicator shaft 169 proximal of the main balloon 160. The torus 161 is preferably a filled polymer, acting as a radiation shield that is deployed as the balloon 160 is inflated.

Figure 16:
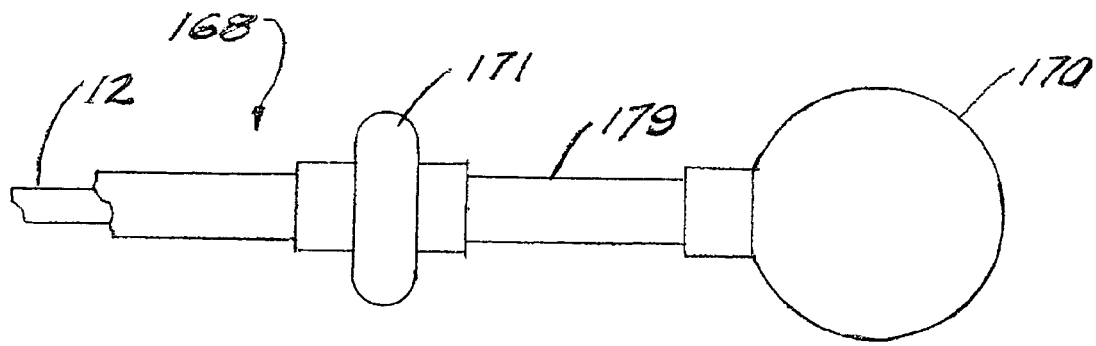
FIG. 16 is a side elevation view of a balloon applicator and source having an independently inflatable collar mounted on the shaft of the applicator.

The embodiment 168 of FIG. 16 is similar to that of FIG. 15, but in this instance, the torus 171 mounts on an applicator shaft 169 proximal of main balloon 170. With appropriate accommodation for inflation, as for example by a separate tube outside the applicator shaft, the torus 171 can be movable on shaft 169. It could also be fixed axially, and have an internal inflation as has been described for the main balloons. This torus is also preferably of a filled polymer.

Figure 17:
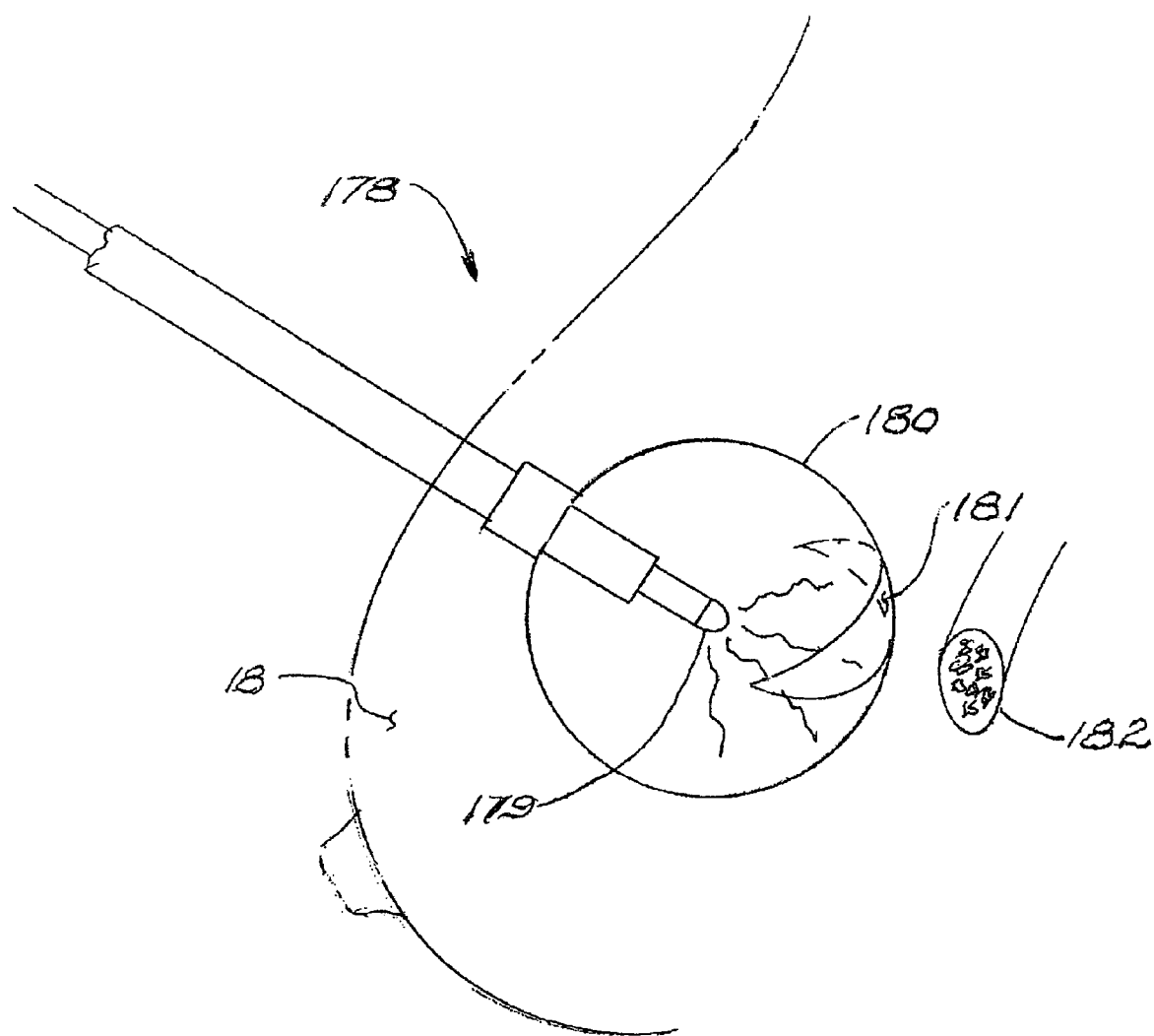
FIG. 17 is a schematic view of a balloon applicator positioned within breast tissue in the vicinity of a bone (rib) wherein the balloon has a shielding segment positioned adjacent to the bone so as to protect the bone from radiation.

FIG. 17 shows an applicator 178 similar to the apparatus described in FIGS. 1a, 1b and FIG. 10, except that a segment 181 of the balloon 180 is made attenuating by adding attenuating material to one portion of the balloon. The applicator is shown within breast tissue 178, and adjacent to a bone, in this example, a rib 182, with the attenuating material situated between the source 179 and the rib.

Figure 18:
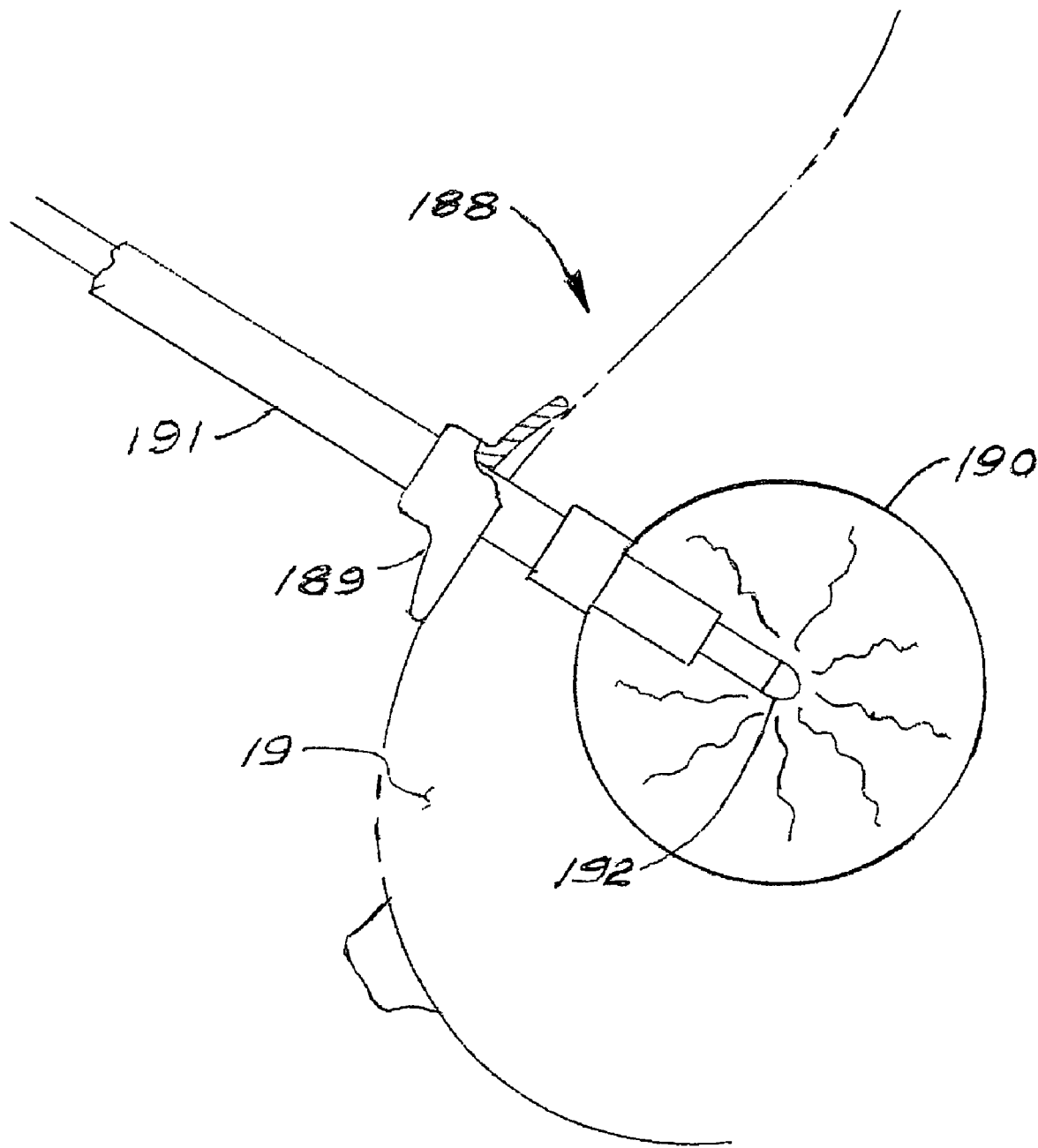
FIG. 18 is a schematic view of an applicator and source positioned within breast tissue and having a solid flange shield as in FIG. 14 positioned on the applicator shaft at the entry into breast tissue.

FIG. 18 shows an applicator 188 with balloon 190 and source 192 within breast tissue 19 and having a solid flange 189 as described in FIG. 14 (to the left) mounted on the applicator shaft 191. The flange 189 in this embodiment is shown slightly cupped to conform to the breast surface. In other applications, the flange may optionally be shaped to accommodate different anatomy.

An important feature of most of the above embodiments is that a radiation shield is included on an applicator, the shield having radiation attenuating properties that vary with position. Such variation with position includes positions beyond the shield, where no attenuation occurs, and includes positions where a hole may occur in a shield, for zero attenuation at that hole or window. Thus, variation with position is intended to include a simple shield wherein the x-ray source is positioned so as to have its radiation attenuated by the shield or positioned so as not to have its radiation attenuated.

The above described preferred embodiments are intended to illustrate the principles of the invention, but not to limit its scope. Other embodiments and variations to these preferred embodiments will be apparent to those skilled in the art and may be made without departing from the spirit and scope of the invention as defined in the following claims.

We claim:

1. A radiation brachytherapy applicator with selective shielding, comprising:

an applicator with a shaft capable of being positioned within a living patient, the shaft having a lumen within which is positioned an electronic x-ray source, near a distal end of the applicator, the x-ray source being controllable on/off and as to depth of penetration of radiation, a shield in the applicator in a generally cylindrical shape and generally surrounding the x-ray source, the shield having radiation attenuating properties that vary with position, and the shield and x-ray source being relatively movable by manipulation from a location proximal of the source and outside the patient, the x-ray source being movable axially relative to the shield, including positions extending out beyond a distal end of the shield and positions within the shield, whereby change of position of the shield relative to the x-ray source changes the pattern of radiation emanating from the applicator and administered to the patient's tissue.

2. The applicator of claim 1, wherein the shield is formed in varying thickness so as to attenuate source radiation to a greater extent at thicker portions and to a lesser extent at thinner portions.

3. The applicator of claim 2, wherein the thickness of the shield is stepped such that as the position of the source changes axially relative to the shield the attenuation of radiation is varied.

4. The applicator of claim 2, wherein the shield is tapered in thickness such that as the position of the source changes axially relative to the shield the attenuation of radiation is varied.

5. The applicator of claim 1, wherein the shield has an opening and is rotatable relative to the source and to the patient's tissue to be irradiated.

6. The applicator of claim 1, wherein the shield and has a self-closing distal end which opens when the shield is retracted and the distal end is pulled back and spread outwardly by engagement with the exterior of the x-ray source, and wherein the distal end of the shield has self-closing elements that close together when the shield is extended such that the distal end is distal of an end of the x-ray source.

7. The applicator of claim 1, wherein the shield has an obliquely angled open distal end, and the shield being rotatable relative to the x-ray source such that, with the x-ray source positioned to partially extend out the open distal end of the shield, rotation of the shield will control the direction of radiation transmission from the source.

8. The applicator of claim 7, wherein the shield is also movable axially relative to the x-ray source.

9. The applicator of claim 1, wherein the applicator includes an inflatable balloon affixed to the shaft, with the shaft including a balloon inflation lumen.

10. The applicator of claim 2, wherein the applicator includes an inflatable balloon affixed to the shaft, with the shaft including a balloon inflation lumen.

11. The applicator of claim 1, wherein the applicator includes an inflatable balloon affixed to the shaft, with the shaft including a balloon inflation lumen.

12. The applicator of claim 5, wherein the applicator includes an inflatable balloon affixed to the shaft, with the shaft including a balloon inflation lumen.

13. The applicator of claim 7, wherein the applicator includes an inflatable balloon affixed to the shaft, with the shaft including a balloon inflation lumen.

14. A radiation brachytherapy applicator with selective shielding, comprising:

an applicator with a shaft capable of being positioned within a living patient, the shaft having a lumen within which is positioned an electronic x-ray source, near a distal end of the applicator, the x-ray source being controllable on/off and as to depth of penetration of radiation, a shield in the applicator and generally surrounding the x-ray source, the shield having radiation attenuating properties that vary with position, and the shield and x-ray source being relatively movable by manipulation from a location proximal of the source and outside the patient, the shield comprising a series of fingers or paddles positioned generally in an arcuate pattern on the applicator so as to be capable at least partially surrounding the x-ray source, the fingers or paddles being oriented parallel to the shaft and side by side and non-collinear with one another so that together the fingers or paddles define essentially a cylindrical array circumscribing a space within which the x-ray source can be positioned, each finger or paddle being individually axially movable parallel to the shaft to extend or retract the finger or paddle from a control position outside the patient to shield radiation from the x-ray source in directions as selected, whereby change of position of one or more of the fingers or paddles relative to the x-ray source changes the pattern of radiation emanating from the applicator and administered to the patient's tissue.

15. The applicator of claim 14, wherein the fingers or paddles are movable via hydraulic connections to the position outside of the patient.

16. The applicator of claim 14, wherein the applicator includes an inflatable balloon affixed to the shaft, with the shaft including a balloon inflation lumen.

* * * * *